US00PP31837P2

(12) United States Plant Patent
Yencho et al.

(10) Patent No.: US PP31,837 P2
(45) Date of Patent: Jun. 2, 2020

(54) SWEETPOTATO PLANT NAMED 'NCORNSP-024SCRI'

(50) Latin Name: ***Ipomoea batatas* (L.) Lam.**
Varietal Denomination: NCORNSP-024SCRI

(71) Applicant: North Carolina State University, Raleigh, NC (US)

(72) Inventors: George Craig Yencho, Raleigh, NC (US); Kenneth Vincent Pecota, Raleigh, NC (US); Meri K. Reeber, Apex, NC (US); Dominic Alexander Gillooly, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/501,233

(22) Filed: Mar. 8, 2019

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
*Assistant Examiner* — Karen M Redden
(74) *Attorney, Agent, or Firm* — Myers Bigel, P.A.

(57) ABSTRACT

'NCORNSP-024SCRI' is a compact, non-twining, upright variety producing many short shoots. It is distinguishable from other cultivars by its purple palmate shaped leaves with a lobed base; a compact habit and semi-erect mounding plant architecture. The purple leaves, short internodes, and the plant architecture are what makes 'NCORNSP-024SCRI' unique amongst the current ornamental sweetpotatoes in the marketplace. 'NCORNSP-024SCRI' also exhibits very good vigor and is well branched.

5 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'NCORNSP-024SCRI'.

BACKGROUND OF THE INVENTION

*Ipomoea batatas* is a member of the morning glory family Convolvulaceae. This species is grown worldwide and it exhibits a wide range of plant forms and colors. The cultivated members of *Ipomoea batatas* grown by farmers worldwide are commonly produced for consumption of their nutritious, enlarged storage roots. These types typically produce a fast growing green vine that has a wide variety of leaf shapes ranging from palmate and deeply lobed, to cordate or triangular shaped leaves with no lobes.

Like their edible forms, *Ipomoea batatas* ornamental sweetpotato plants are a heat-loving, drought-tolerant, perennial vine typically grown as an annual. However, ornamental sweetpotato plants are distinguished from the edible cultivated forms in that they often do not produce attractive, enlarged storage roots suitable for human consumption. Instead they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g. pale yellow to dark purple with some exhibiting temporal and individual leaf color variegation patterns) and plant shapes (e.g. mounded and very compact to prostrate and highly spreading). They can be grown as a potted plant and/or in a mixed planting format, and they have the ability to cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

To meet the growing horticultural demand for ornamental sweetpotatoes, it is desirable to produce new cultivars of ornamental sweetpotato with new or improved foliage colors, variegation patterns, leaf shapes, and plant architectures. In addition, it would be advantageous to develop cultivars of ornamental sweetpotato exhibiting a more compact growth that do not out-compete other species in mixed containers.

'NCORNSP-024SCRI' was bred to meet the increasing demand for new ornamental sweetpotatoes. 'NCORNSP-024SCRI' is a compact, non-twining, upright variety producing many short shoots. It is distinguishable from other cultivars by its purple palmate 3-5 moderately lobed leaves, a compact habit and semi-erect mounding plant architecture. The purple leaves, short internodes, and the plant architecture, which promotes good plant production in the greenhouse for wholesale distributors, distinguishes 'NCORNSP-024SCRI' amongst the current ornamental sweetpotatoes in the marketplace. 'NCORNSP-024SCRI' exhibits very good vigor and is very well branched. In greenhouse and field trials conducted since 2015 'NCORNSP-024SCRI' has been shown to be much less vigorous than *Ipomoea batatas* 'Margarita' (unpatented) and 'Blackie' (unpatented) and is suitable for use as a landscape or containerized plant. The production of flowers by 'NCORNSP-024SCRI' is infrequent under short day conditions.

Lineage. 'NCORNSP-024SCRI' (breeding designation NC8827-031ORN) originated from open-pollinated seed from the proprietary *Ipomoea batatas* breeding line NC8226-011ORN (the female parent; not patented). Botanical seed was harvested from this and other ornamental sweetpotato lines planted in our summer advanced ornamental replicated trials between June of 2014 and November of 2014 in Clinton, N.C. NC8826-011ORN resulted from open pollinated seed harvested from the proprietary *Ipomoea batatas* breeding line NC7409-060ORN (the female parent; not patented). Botanical seed from NC8226-011ORN was planted in the greenhouse in December 2015. The first cycle of selection on the seedlings was exercised at the seedling tray stage and survivors were transferred to a single 6-inch pot, which was then maintained in the greenhouse. Cuttings (2 each) were taken from the plants in April and planted in the field as 2-plant, unreplicated plots, during mid-June 2015. The single, individual plant now known as 'NCORNSP-024SCRI' was selected Aug. 20, 2015 because of its combination of exceptional features, and it has been propagated asexually as vegetative material from the original 6-in pot in the sweetpotato breeding greenhouse and via tissue culture in Raleigh, N.C. since that time.

Asexual Reproduction. Since its selection, *Ipomoea batatas* 'NCORNSP-024SCRI' has been asexually reproduced in North Carolina predominantly by vegetative propagation of vine cuttings. Successively, there have been six cycles of vegetative propagation, one cycle of tissue culture micropropagation, and multiple vegetative propagation cycles to increase plant numbers. Asexual reproduction of 'NCORNSP-024SCRI' by cuttings has shown that the unique features of the new cultivar are stable and that the plant reproduces true to type in successive generations.

SUMMARY OF THE INVENTION

'NCORNSP-024SCRI' is a compact, non-twining, semi-upright variety producing many short shoots. It is distinguishable from other *Ipomoea batatas* cultivars by its dark purple, palmate moderately lobed leaves with 3-5 lobes; a compact habit and semi-erect mounding plant architecture. The dark purple leaves, short internodes, and the plant architecture distinguishes 'NCORNSP-024SCRI' amongst the current ornamental sweetpotatoes in the marketplace. 'NCORNSP-024SCRI' also exhibits very good vigor and is very well branched, a growth habit that promotes good plant production in the greenhouse for wholesale distributors. In greenhouse and field trials conducted since 2015 by the breeding program and industry collaborators 'NCORNSP-024SCRI' has been shown to be a much less vigorous vine producer than *Ipomoea batatas* 'Margarita' and 'Blackie' and is suitable for use as a landscape or containerized plant. The production of flowers by 'NCORNSP-024SCRI' is sporadic under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which more accurately describe the colors of the new *Ipomoea batatas.*

DETAILED BOTANICAL DESCRIPTION OF THE NEW VARIETY

Figure 1A:
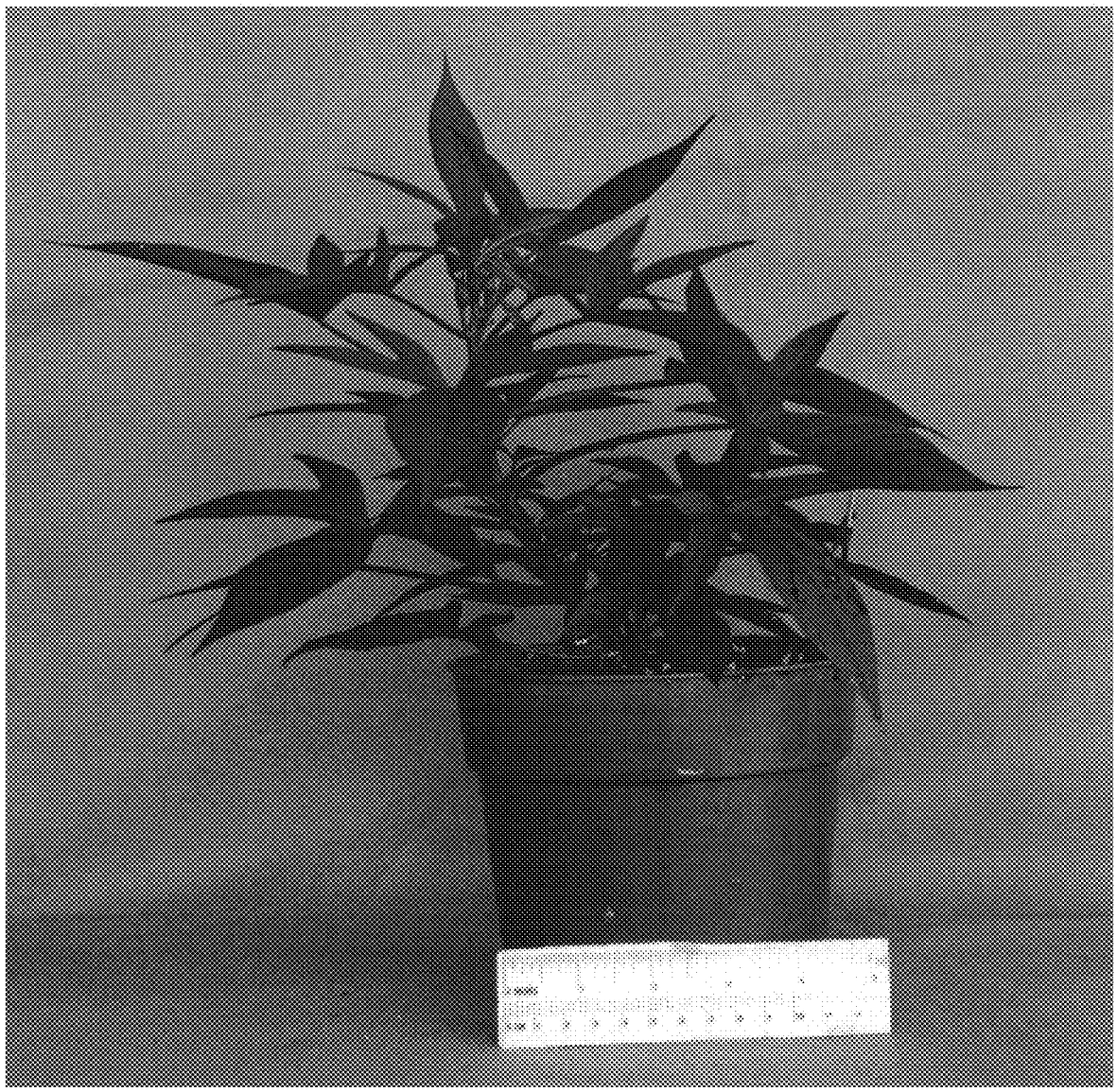
FIGS. 1A-1B. Color photograph of a typical specimen of greenhouse grown *Ipomoea batatas* 'NCORNSP-024SCRI' in a 6-inch pot from the side (FIG. 1A) and top (FIG. 1B), 59 days after planting.
Figure 1B:
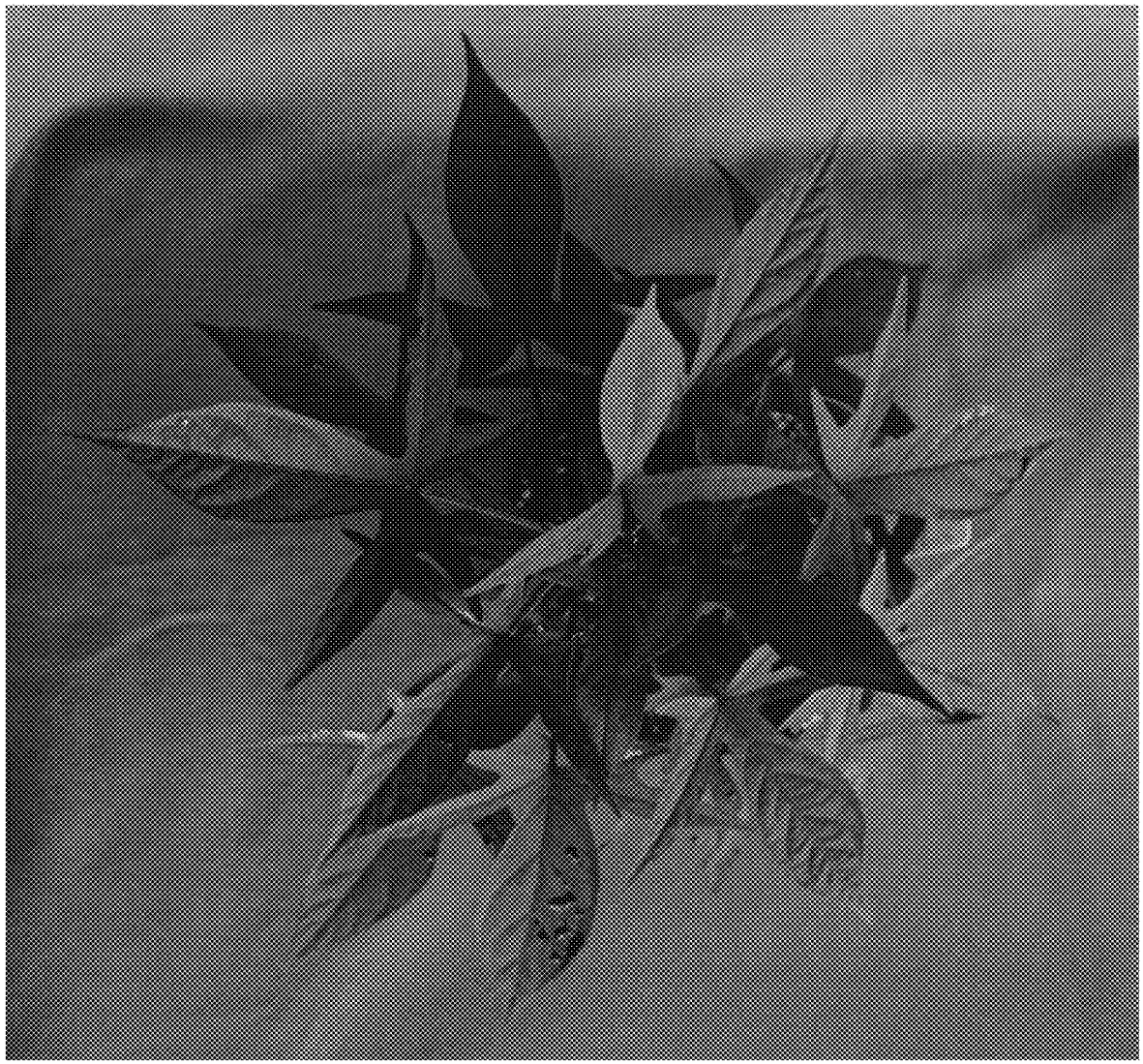
Figure 2A:
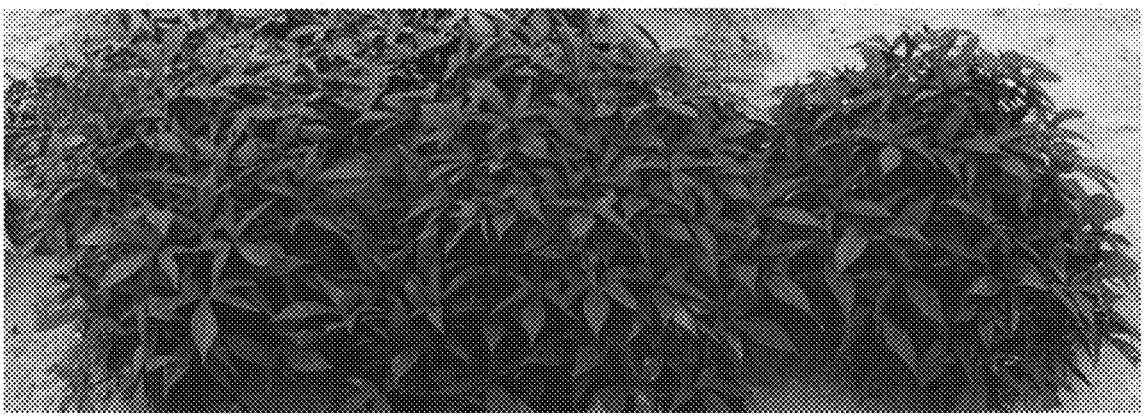
FIGS. 2A-2B. Color photograph of a typical specimen of *Ipomoea batatas* 'NCORNSP-024SCRI' from side (FIG. 2A) and top (FIG. 2B) in the field, 68 days after planting.
Figure 2B:
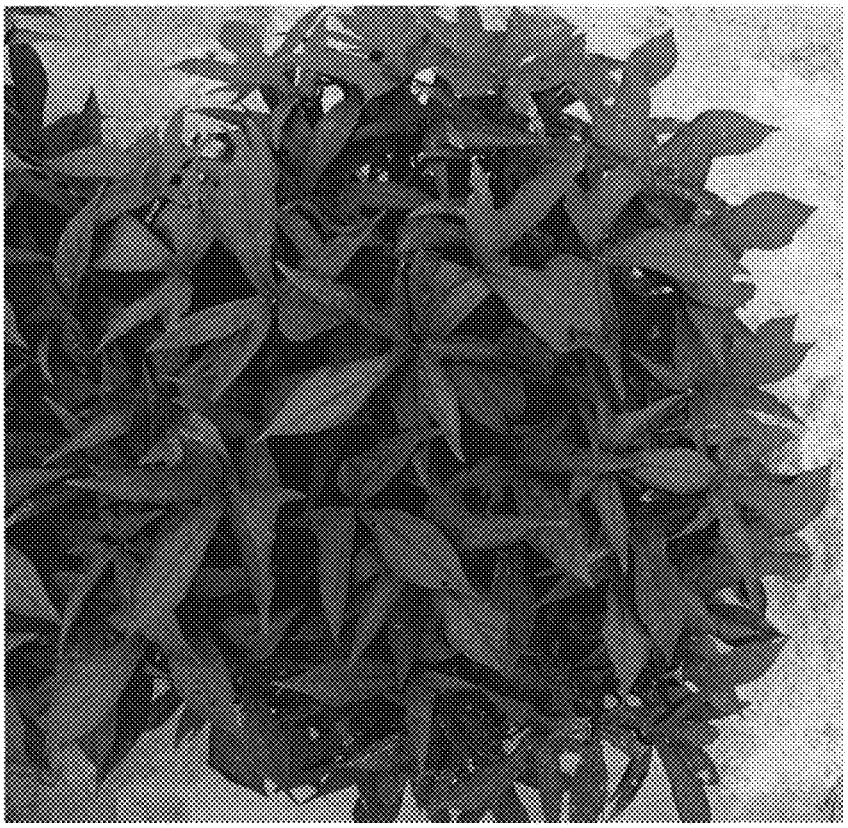
Figure 3A:
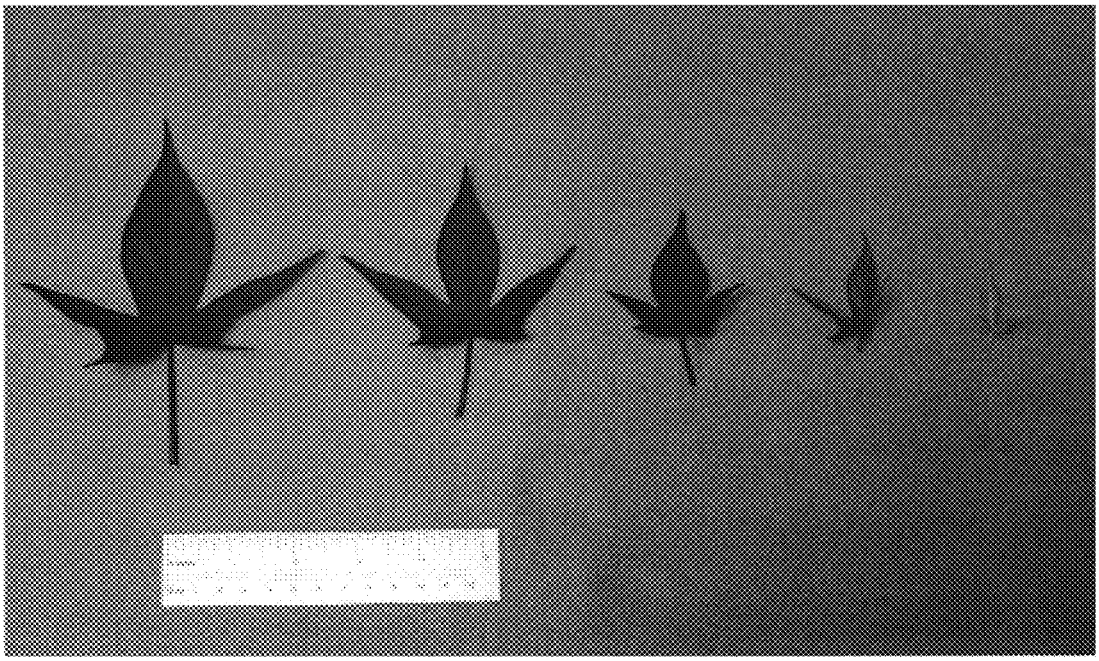
FIGS. 3A-3B. Color photograph showing upper (FIG. 3A) and lower (FIG. 3B) surfaces of immature (right) to mature (left) leaves produced by *Ipomoea batatas* 'NCORNSP-024SCRI'.
Figure 3B:
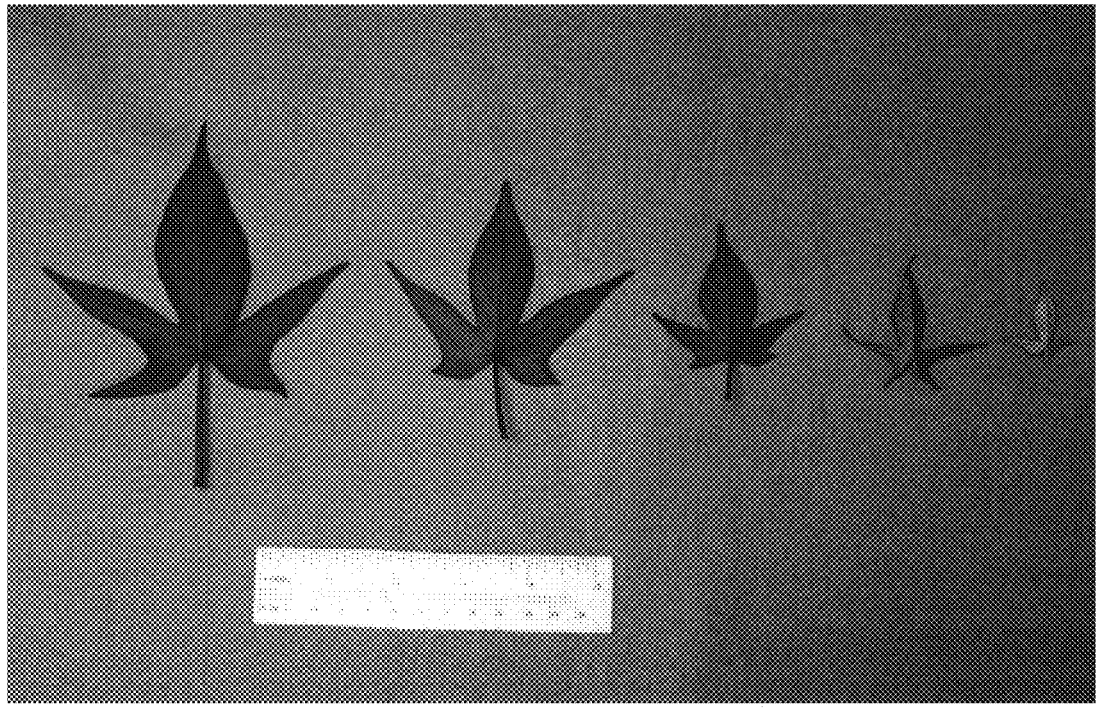

The following is a detailed description of the botanical characteristics of a new and distinct cultivar of *Ipomoea batatas* plant known by the cultivar name 'NCORNSP-024SCRI'. All colors cited herein refer to The Royal Horticulture Society Colour Chart designations (The Royal Horticultural Society, London, 1995, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134pp.). Where dimensions, sizes, colors, and other characteristics are given, it is to be understood that such characteristics are approximations or averages set forth as accurately as practicable.

The descriptions reported herein are from a group of 59-day-old specimens grown individually in six-inch azalea pots. The plants were grown in Raleigh, N.C., under commercial practice in a glass-covered greenhouse, where, during the fall, day and night temperatures range between 30-40° C. and 22-26° C., respectively. After rooting, plants were treated with 200 ppm 20-10-20 fertilizer weekly. Plant histories were taken in December 2017 in Raleigh, N.C. *Ipomoea batatas* 'NCORNSP-024SCRI' has not been observed under all possible environmental conditions; therefore, the phenotype may vary under different environmental conditions such as season, temperature, light intensity, day length, cultural conditions, and the like, without however, any variance in the genotype.

Classification.

*Botanical name.*—*Ipomoea batatas* (L.) Lam.

*Common name.*—Ornamental Sweetpotato.

*Variety name.*—'NCORNSP-024SCRI'.

Growth conditions: *Ipomoea batatas* 'NCORNSP-024SCRI' has very good vigor and a moderate growth rate. In locations with mild winter conditions, *Ipomoea batatas* 'NCORNSP-024SCRI' will grow perennially; otherwise it is an annual plant. Similar to other cultivated sweetpotatoes, wind or rain rarely causes much damage to 'NCORNSP-024SCRI', but if damage does occur, the plant drops the damaged leaves and grows new shoots at nodes where the leaves were lost. Under low light levels in a greenhouse, 'NCORNSP-024SCRI' can develop intumescence, which will remain on the affected foliage, but will be outgrown with new foliage.

Aboveground structure and coloration: FIGS. 1A, 1B, 2A, 2B, 3A and 3B show the shape and coloration of a typical specimen of *Ipomoea batatas* 'NCORNSP-024SCRI'. Color will vary somewhat due to temperature and nutrient stress. Overall, this cultivar is a compact, non-twining, semi-upright herbaceous plant that has an average height of ~15.6 cm and an average area spread of ~33.3 cm. The growth habit of this plant is to grow upright with shoots growing upward and outward.

Branches:

*Branching habit.*—Freely-branching with ~3-4 primary lateral branches coming off of the stem. Very dense foliage and no pinching is required to stimulate branching. Branch texture is smooth and glabrous with slight pubescence.

*Vegetative lateral branching*.—Length: ~16.9 cm. Diameter: ~0.5 cm. Internodes are short with an average length of ~1.6 cm.

*Secondary lateral shoots*.—No measurable secondary lateral shoots formed on the rated plants.

*Stem*.—Round and smooth with an upward, very strong, slightly flexible, non-brittle strength. Color: Purple (RHS N77A).

*Adventitious roots*.—Present at nodes. Color: purple (RHS N77A) with yellow (RHS N144B).

*Petiole*.—Petioles are held slightly upward and curve outward. Leaf petiole has a smooth glabrous texture. Length: ~9.3 cm. Diameter: ~0.3 cm. Color: Purple (RHS N186B-A).

Foliage: Leaves are alternate and tend to slightly spiral around the stem. They are simple and moderately divided into 5 lobes. Leaf shape is somewhat variable as is size (see FIGS. 3A-3B).

*Quantity*.—Heavily foliated, with ~20.5 leaves per lateral branch.

*Mature leaf length*.—~12.4 cm.

*Mature leaf width*.—~13.8 cm.

*Leaf margin*.—Entire.

*Leaf apex*.—Acuminate.

*Leaf base*.—Lobed.

*Leaf texture*.—Glabrous texture and matte finish.

*Venation*.—Arcunate to cross-venulate. Texture: Glabrous.

*Color*.—Leaves are purple and range within that palate as they mature. See also Table 1.

TABLE 1

Leaf color of *Ipomoea batatas* 'NCORNSP-024SCRI'.

| Leaf Structure | Upper Surface | Lower Surface |
|---|---|---|
| Young Leaf | Greyed Purple (RHSN186B-A) | Purple (RHS N77A-N79A) |
| Mature Leaf | Greyed Purple (RHS N186A) | Greyed Purple (RHS N186B) |
| Vein-mature leaf | Greyed Purple (RHSN186B-A) | Purple (RHS N77C-D) |
| Vein-young leaf | Greyed Purple (RHSN186B-A) | Purple (RHS N77C-D) |

Inflorescence: The production of flowers by 'NCORNSP-024SCRI' is very sporadic under short day conditions and we have not been able to obtain flowers for the measurement of flower traits.

Figure 4:
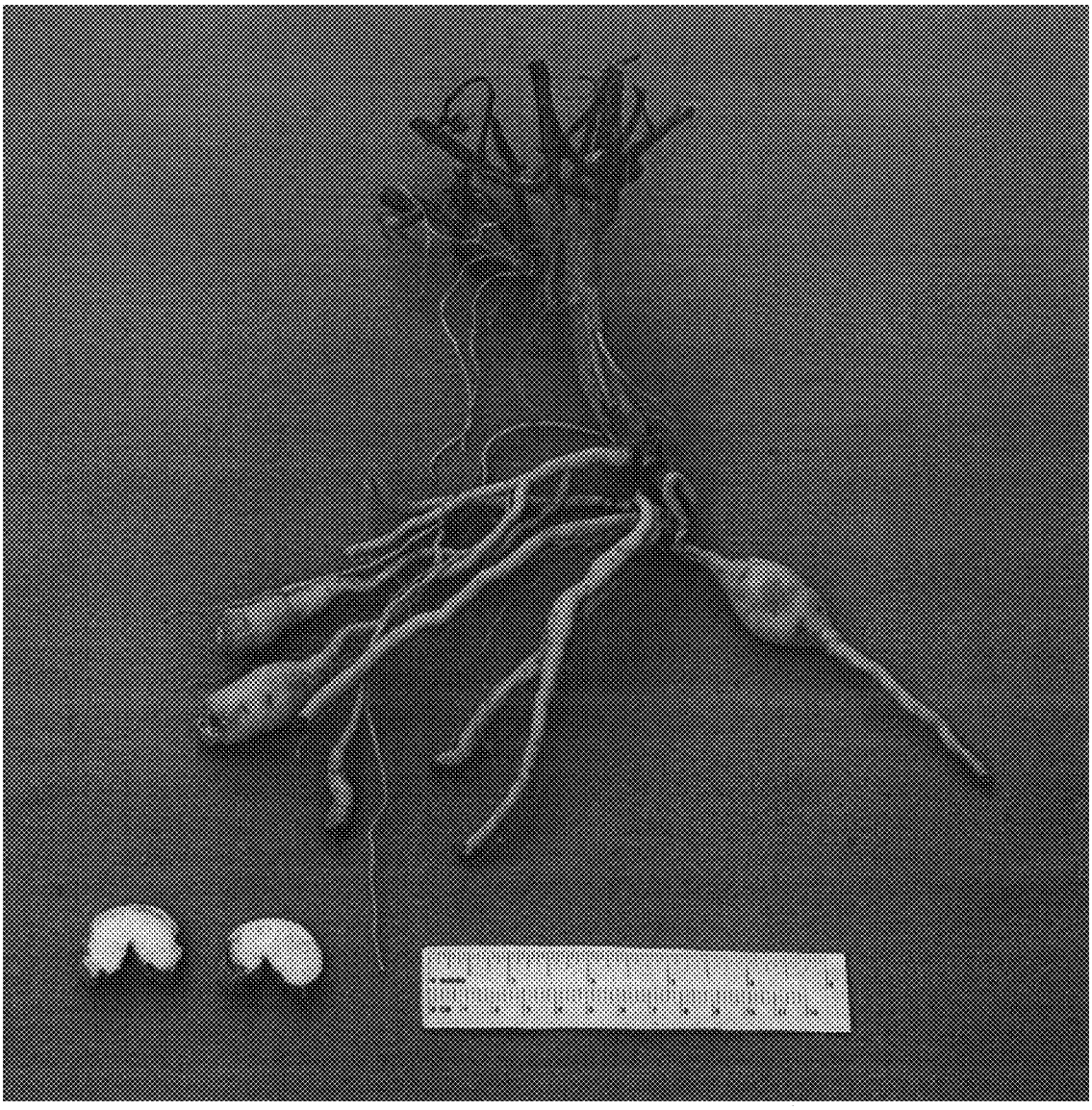
FIG. 4 is a color photograph showing the storage roots produced by *Ipomoea batatas* 'NCORNSP-024SCRI' in the field, 133 days after planting.

Storage root coloration: Plants form no, to small, underground storage roots that are typically malformed and do not meet USDA Sweetpotato Storage Root Grade Standards (see FIG. 4). Fibrous roots are typically cream colored (RHS 155B). Storage roots that are formed possess greyed yellow (RHS 162C) skin and a yellow flesh (RHS 11D).

Disease or pest resistance. 'NCORNSP-024SCRI' is susceptible to whiteflies (*Trialeurodes vaporarium*) and thrips (order Thysanoptera) in a greenhouse environment. 'NCORNSP-024SCRI' is susceptible to damage by Japanese beetles (*Popilla japonica*) under outdoor conditions. The resistance or susceptibility of 'NCORNSP-025SCK' to other known insects and pathogens of sweetpotato is unknown. Under low light conditions, slight edema may occur.

Comparison with parent plant NC8226-011ORN: 'NCORNSP-024SCRI' (aka NC8827-031ORN) has deeply lobed leaves and dark purple foliage, while NC8226-011ORN, the maternal parent, has slightly toothed, heart-shaped leaves, and NC8226-011ORN has a more compact growth habit compared to 'NCORNSP-024SCRI'. The paternal parent of NC8226-011ORN is unknown, as it came from an open pollinated seed.

Comparison with other *Ipomoea batatas* cultivars: 'NCORNSP-024SCRI' is distinct based on leaf shape and plant architecture. Of the common cultivars of ornamental sweetpotato, 'NCORNSP-024SCRI' is best compared with the cultivars 'Sweet Caroline Purple' (U.S. Plant Pat. No. 14,912) and 'NCORNSP-015SCPI' (U.S. Plant Pat. No. 23,631) (Table 2). Like 'Sweet Caroline Purple', 'NCORNSP-024SCRI' has purple leaves. However, the leaves of 'NCORNSP-024SCRI' are slightly larger and they possess a deeper purple coloration that is more consistent throughout the plant foliage. The habit of 'NORNSP-024SCRI' is also more compact and upright than either 'NCORNSP-015SCPI' (U.S. Plant Pat. No. 23,613) or 'Sweet Caroline Purple'.

'NCORNSP-024SCRI' has a moderately compact to compact, semi-upright, non-twining plant habit compared with the moderately compact, slightly trailing habit of 'Sweet Caroline Purple' and the compact, upright, non-twining habit of 'Sweet Caroline Bewitched Imp' ('NCORNSP-014BWPI'; patented (U.S. Plant Pat. No. 23,651)). Furthermore, 'NCORNSP-024SCRI' has a larger average leaf size compared with the smaller leaves of 'NCORNSP-019SC-SHLM' (U.S. Plant Pat. No. 28,318). Unlike 'Sweet Caroline Bewitched Imp', which does not produce flowers, even under short-day conditions, 'NCORNSP-024SCRI' will flower sporadically throughout the season.

TABLE 2

Comparison of 'NCORNSP-024SCRI' with other *Ipomoea batatas* cultivars.

| Characteristic | 'NCORNSP-024SCRI' | 'Sweet Caroline Sweetheart Purple' (U.S. Plant Pat. 14,912) | 'NCORNSP-015SCPI' |
|---|---|---|---|
| Plant Habit | Moderately Compact to Compact, Upright, Semi-erect | Moderately Compact, Slightly Trailing | Moderately Compact, Slightly-Upright |
| Average Leaf Length and Width | Length: 12.4 cm Width: 13.8 cm | Length: 11.5 cm Width: 8.0 cm | Length: 13.3 cm Width: 13.2 |
| Foliage Color | Greyed Purple (RHS N186A) | Purple with green base (RHS N77A, 147A) | Dark purple (RHS N186A-187A) |
| Leaf Shape | Moderately lobed, 5 lobes. Entire with and acuminate apex and a lobed base. | Moderately Lobed, 5-7 lobes. Entire with acute apex and acute base. | Moderately Lobed, 3-5 lobes. Entire with and acuminate to acute apex and cordate base. |

We claim:

1. A new and distinct cultivar of *Ipomoea batatas* plant named 'NCORNSP-024SCRI', substantially as illustrated and described herein.

* * * * *